United States Patent [19]
Lopotar et al.

[11] Patent Number: 5,962,661
[45] Date of Patent: Oct. 5, 1999

[54] SECO COMPOUNDS FROM THE CLASS OF TYLOSINS

[75] Inventors: Nevenka Lopotar; Amalija Narandja; Zoran Mandić, all of Zagreb, Croatia

[73] Assignee: Pliva, Farmaceutska, Kemijska, Prehrambena i Kozmeticka Industrija, Dionicko Drustvo, Zagreb, Croatia

[21] Appl. No.: 09/114,514

[22] Filed: Jul. 14, 1998

[30] Foreign Application Priority Data

Jul. 16, 1997 [HR] Croatia .................................. P970386
May 22, 1998 [HR] Croatia .................................. P980276

[51] Int. Cl.⁶ .................................................. C07H 15/00
[52] U.S. Cl. .......................................... 536/17.9; 536/124
[58] Field of Search ...................... 536/17.9, 124

[56] References Cited

U.S. PATENT DOCUMENTS 5,023,240  6/1991  Narandja et al. ........................ 514/30

FOREIGN PATENT DOCUMENTS

0410433 A2  1/1991  European Pat. Off. .

*Primary Examiner*—Kathleen K. Fonda
*Attorney, Agent, or Firm*—Pollock, Vande Sande & Amernick

[57] ABSTRACT

Seco compounds from a class of tylosins represented by the formula I wherein
R stands for H or $CH_3$,
$R^1$ stands for H, $CH_3$, $C_1$–$C_3$ acyl or aryl sulfonyl,
$R^2$ stands for H and $R^3$ stands for $NH_2$ or OH, or $R^2$ and $R^3$ together stand for =O or =NOH,
$R^4$ stands for H or $C_1$–$C_3$ acyl,
and the line - - - stands for a double or a single bond, and to a process for their preparation are provided.

Oximation of 4'-demicarosyl-8a-aza-8a-homorelymycin causes breaking of the lactam to obtain a seco compound. The seco compound can be subjected to reductive N-alkylation or to conversion of the hydroxyimino group into a keto group and then optionally to N- or N,O-acylation, a catalytical hydrogenation of the double bond or a reduction of the ketone or a reduction of the hydroxyimino group into an amino group.

21 Claims, No Drawings

SECO COMPOUNDS FROM THE CLASS OF TYLOSINS

TECHNICAL FIELD OF THE INVENTION

IPC: A 61 K 31/70 C 07 H 17/08

TECHNICAL PROBLEM

The invention relates to novel seco compounds from the class of tylosins, potential intermediates in the preparation of novel azalide antibiotics, as well as to processes for their preparation.

Specifically, the invention relates to linear 8a-secoazalides of the general formula I

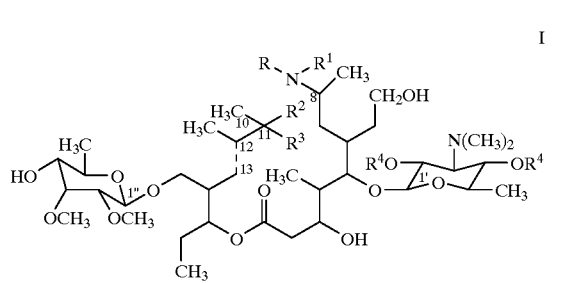

wherein
  R stands for H or $CH_3$,
  $R^1$ stands for H, $CH_3$, $C_1$–$C_3$ acyl or aryl sulfonyl,
  $R^2$ stands for H and $R^3$ stands for $NH_2$ or OH, or $R^2$ and $R^3$ together stand for =O or =NOH,
  $R^4$ stands for H or $C_1$–$C_3$ acyl,
  and the line - - - stands for a double or a single bond.

PRIOR ART

It is known that C-9 oximes of tylosine and of derivatives thereof have already been prepared (Narandja, A. et al., EP 0 287 082 B1). It is known as well that by a Beckmann rearrangement of oximes of tylosine and of derivatives thereof 8a-aza- and 9a-aza-regioisomeric lactams were obtained (Lopotar, N. et al., EP 0 410 433 B1). It is also known that by alkaline alcoholysis of tylosine derivatives a breaking of lactones and the formation of corresponding esters of secoacids takes place (Fishman, A. G. et al., J. Chem. Soc. Perkin Trans. I, 799–805, 1989).

It has been now found that by oximation of 8a-aza-derivatives of tylosine an opening of lactarns takes place, whereby carbonyls are cleaved and novel hitherto not described 8a-secoazalides are formed.

DETAILED DESCRIPTION OF THE INVENTION

According to the present invention novel 8a-secoazalides of the general formula I,

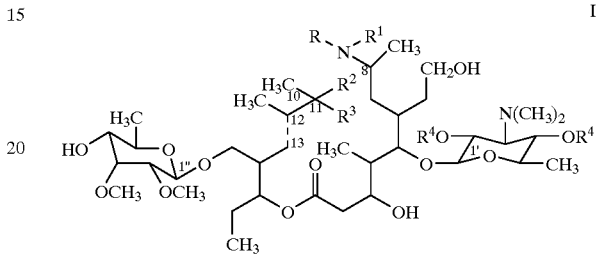

wherein

R stands for H or $CH_3$ $R^1$ stands for H, $CH_3$, $C_1$–$C_3$ acyl or aryl sulfonyl, $R^2$ stands for H and $R^3$ stands for $NH_2$ or OH, or $R^2$ and $R^3$ together stand for =O or =NOH, $R^4$ stands for H or $C_1$–$C_3$ acyl, and the line - - - stands for a double or a single bond, can be prepared in such a way that 4'-demicarosyl-8a-aza-8a-homorelomycin of the formula II

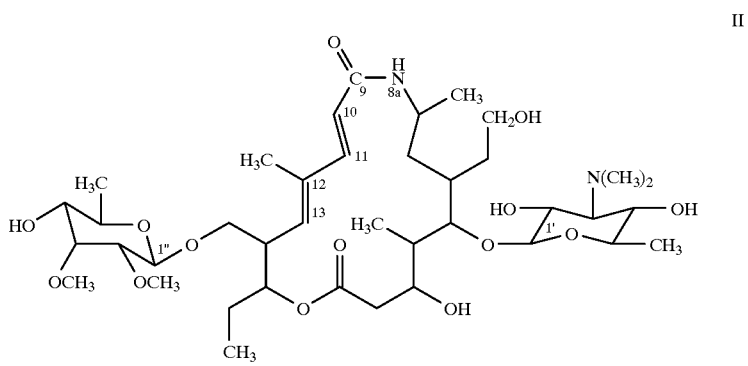

A/ is subjected to a reaction of oximation with hydroxylamine hydrochloride in the presence of organic bases which can simultaneously serve as a solvent and then, optionally, A1/ reductively N-alkylated with a corresponding alkylating agent in the presence of a corresponding reducing agent in a reaction-inert solvent, or, optionally, A2/ subjected to catalytic hydrogenation in the presence of palladium-on-charcoal or, optionally, B/ is subjected to a conversion of hydroxyimino group into keto group by means of corresponding agents in the presence of organic or inorganic acids and then, optionally, B1/ N- or N,O-acylated with acids or their anhydrides or chlorides in a reaction-inert solvent, and then, optionally, B1/1 subjected to solvolysis, or, optionally, B2/ catalytically hydrogenated in the manner of A2 or, optionally, C/ is reduced by complex metallic hydrides and then, optionally, C1/ N-acylated as described in B1, or C2/ reductively N-alkylated as described in A1, or C3/ catalytically hydrogenated in the manner of A2, and then, optionally, C4/ reductively N-alkylated in the manner of A1, or optionally, D/ is subjected to catalytical reduction with Pt (IV) oxide in a reaction-inert solvent, or optionally, E/ an electrochemical reduction is performed.

The reaction of oximation of 4'-demicarosyl-8a-aza-8a-homorelomycin is carried out with 3 to 10 equivalents of hydroxlyamine hydrochloride in pyridine in a nitrogen stream at reflux temperature during 3 to 10 hours, whereby a compound of the general formula I is obtained, wherein R, $R^1$ and $R^4$ are the same and stand for H, $R^2$ and $R^3$ together stand for NOH and the line - - - stands for a double bond.

The reaction of reductive N-alkylation of the above cited compound and of the compounds of the general formula I, wherein R, $R^1$, $R^2$ and $R^4$ are the same and stand for H, $R^3$ stands for OH and the line - - - stands for a double or a single bond, is carried out with 1 to 4 equivalents of formaldehyde (36%) in the presence of a 1–5 fold amount of formic acid (98–100%) in halogenated hydrocarbons, preferably in chloroform or methylene chloride, at a temperature from 10° C. to reflux temperature during 2 to 30 hours, whereby compounds of the general formula I are obtained, wherein R and $R^1$ are the same and stand for $CH_3$, $R^2$ and $R^3$ together stand for NOH, $R^4$ stands for H and the line - - - stands for a double bond, or R and $R^1$ are the same and stand for $CH_3$, $R^2$ and $R^4$ are the same and stand for H, $R^3$ stands for OH and the line - - - stands for a double or a single bond.

The reaction of conversion of hydroxyimino group of the compound of the general formula I, wherein R, $R^1$ and $R^4$ are the same and stand for H, $R^2$ and $R^3$ together stand for NOH and the line - - - stands for a double bond, is carried out with $NaHSO_3$ in the presence of an acid, preferably formic acid (98–100%), in 50% ethanol at reflux temperature during 2 to 8 hours, whereby a compound of the general formula I is obtained, wherein R, $R^1$ and $R^4$ are the same and stand for H, $R^2$ and $R^3$ together stand for O and the line - - - stands for a double bond.

The reaction of N- or N,O-acylation of the compounds of the general formula I, wherein R, $R^1$ and $R^4$ are the same and stand for H, $R^2$ and $R^3$ together stand for O, or R, $R^1$, $R^2$ and $R^4$ are the same and stand for H, R3 stands for OH, and the line - - - stands for a double bond, is carried out with $C_1$–$C_3$ carboxylic acids, preferably with formic acid (98–100%) and acid anhydrides, preferably with acetic acid anhydride in halogenated hydrocarbons, preferably in chloroform or methylene chloride or in acid chlorides, preferably with tosyl chloride in pyridine, at room temperature or reflux temperature during 1 to 20 hours, whereby the compounds of the general formula I are obtained, wherein R and $R^4$ are the same and stand for H, $R^1$ stands for CHO, $R^2$ and $R^3$ together stand for O, or R stands for H, $R^1$ and $R^4$ are the same and stand for $COCH_3$, $R^2$ and $R^3$ together stand for O, or R, $R^2$ and $R^4$ are the same and stand for H, $R^1$ stands for tosyl, $R^3$ stands for OH and the line - - - stands for a double bond.

The solvolysis of the compounds of the general formula I, wherein R stands for H, $R^1$ and $R^4$ are the same and stand for $COCH_3$, $R^2$ and $R^3$ together stand for O, is carried out in methanol at room temperature during 3 days, whereby a compound of the general formula I is obtained, wherein R and $R^4$ stand for H, $R^2$ and $R^3$ together stand for O, $R^1$ stands for $COCH_3$ and the line - - - stands for a double bond.

The catalytical hydrogenation of the compounds of the general formula I, wherein R, $R^1$ and $R^4$ are the same and stand for H, $R^2$ and $R^3$ together stand for NOH or O, or R, $R^1$, $R^2$ and $R^4$ are the same and stand for H, $R^3$ stands for OH, and the line - - - stands for a double bond, is carried out in a $C_1$–$C_3$ aliphatic alcohol in the presence of a noble metal on an inert carrier, preferably with palladium-on-charcoal (2–5 w/w), at a hydrogen pressure from 0.2 to 0.5 MPa and at room temperature during 2 to 10 hours, whereby compounds of the general formula I are obtained, wherein R, $R^1$ and $R^4$ are the same and stand for H, $R^2$ and $R^3$ together stand for NOH or 0, or R, $R^1$, $R^2$ and $R^4$ are the same and stand for H, $R^3$ stands for OH and the line - - - stands for a single bond.

The reduction of the compounds of the general formula I, wherein R, $R^1$ and $R^4$ are the same and stand for H, $R^2$ and $R^3$ together stand for O and the line - - - stands for a double bond, is carried out with complex metallic hydrides, preferably with $NaBH_4$ in a $C_1$–$C_3$ aliphatic alcohol and at room temperature during 30 minutes to 2 hours, whereby a compound of the general formula I is obtained, wherein R, $R^1$, $R^2$ and $R^4$ are the same and stand for H, $R^3$ stands for OH and the line - - - stands for a double bond.

The catalytical reduction of the compounds of the general formula I, wherein R, $R^1$ and $R^4$ are the same and stand for H, $R^2$ and $R^3$ together stand for NOH and the line - - - stands for a double bond, is carried out in glacial acetic acid in the presence of noble metals and their oxides as catalysts, preferably with platinum (IV) oxide at a hydrogen pressure from 5.07 to 70.93 bars and at room temperature during 10 hours to 3 days, whereby a compound of the general formula I is obtained, wherein R, $R^1$, $R^2$ and $R^4$ are the same and stand for H, $R^3$ stands for $NH_2$ and the line - - - stands for a single bond.

The electrochemical reduction of the compound of the general formula I, wherein R, $R^1$ and $R^4$ are the same and stand for H, $R^2$ and $R^3$ together stand for NOH and the line - - - stands for a double bond, is carried out in an electrolytic H-cell with the anode and cathode regions separated by a membrane. A Hg basin is used as the working electrode and graphite is used as the counter electrode. The reaction is carried out in a phosphate buffer pH 4.0–7.0 and at a constant potential between 1.2 –1.6 V against saturated calomel electrode during 1 to 5 hours at room temperature in a nitrogem stream, whereby a compound of the general formula I is obtained, wherein R, $R^1$, $R^2$ and $R^4$ are the same and stand for H, $R^3$ stands for $NH_2$ and the line - - - stands for a double bond.

The structure of the novel compounds was established by spectrometrical methods and mass analysis. The newly prepared 8a-secoazalides contain various reactive terminal functional groups and in practice they are important as intermediates for the synthesis of novel azalide antibiotics with a modified macrocyclic ring.

The invention is illustrated by the following examples, which, however, do not limit the scope of the invention in any way.

EXAMPLE 1

4'-Demicarosyl-10-hydro-11-dehydro-11-hydroxyimino-9-carbonyl-9-nor-8a,9seco-8a-aza-8a-homorelomycin (1)

4'-Demycarosyl-8a-aza-8a-homorelomycin (4.0 g, 5.08 mmoles) was dissolved in dry pyridine (40 ml), $NH_2OH$ HCl (3.2 g, 46.04 mmoles) was added and it was stirred in a nitrogen stream at reflux temperature for 6 hours. The reaction solution was diluted with water (150 ml), alkalized with 10% w/v NaOH to pH 9.0 and evaporated at a reduced pressure to one third of the volume and extracted by means of gradient extraction with $CHCl_3$ at pH 7.0 and 9.5. The combined chloroform extracts at pH 9.5 were dried ($K_2CO_3$) and evaporated under reduced pressure, yielding 2.5 g of a crude product. Chromatography on a silica gel column using the solvent system $CH_2Cl_2$—$CH_3OH$-conc.$NH_4OH$, 90:9:1.5 gave 1.5 g of the TLC homogeneous product (1).

M.p. 83–87° C. TLC: $CH_2Cl_2$—$CH_3OH$-conc. $NH_4OH$ (90:20:2), system A Rf0.214 IR($CHCl_3$) $cm^{-1}$: 1725, 1590, 1450, 1375, 1165, 1065, 960.

$^1$H NMR ($CDCl_3$) δ ppm: 5.70 (H-13), 4.56 (H-1"), 4.41 (H-1'), 3.90 (Ha-20), 3.58 (Hb-20), 3.61 (3"—$OCH_3$), 3.48 (2"—$OCH_3$), 3.09 (H-8), 2.49 /3'-N($CH_3$)$_2$/, 1.99 (H-10), 1.82 (H-22),117 (H-21).

$^{13}$C NMR ($CDCl_3$) δ ppm: 173.3 (C-1), 157.5 (C-11), 135.9 (C-12), 129.3 (C-13), 106.6 (C-1'), 101.0 (C-1"), 61.7 (3"—$OCH_3$), 60.3 (C-20), 59.5 (2"—$OCH_3$), 44.9 (C-8), 41.7 /3'-N($CH_3$)$_2$/, 41.7 (C-7), 35.6 (C-6), 24.1 (C-21), 13.6 (C-22), 10.5 (C-10).

FAB ($MH^+$) 794.

| Analysis: | calc.: | found: |
|---|---|---|
| N | 5.29% | 5.40% |

EXAMPLE 2

4'-Demicarosyl-8a-dimethylamino-10-hydro-11-dehydro-11-hydroxyimino-9-carbonyl-9-nor-8a,9seco-8a-aza-8a-homorelomycin (2)

The compound 1 (0.5 g, 0.63 mmole) was dissolved in $CHCl_3$ (30 ml), formic acid (98–100%) (0.12 ml, 3.2 mmoles) and formaldehyde (36%) (0.12 ml, 1.48 mmole) were added and then it was refluxed for 2 hours under stirring. Upon addition of $H_2O$ (30 ml), a product was isolated by means of gradient extraction with $CHCl_3$ at pH 5.5 and 9.5. The combined chloroform extracts at pH 9.5 were dried ($K_2CO_3$) and evaporated at a reduced pressure and the obtained product was chromatographed on a silica gel column using the solvent system $CH_2Cl_2$-$CH_3OH$-conc.$NH_4OH$, 90:9:1.5, yielding 0.4 g of the TLC homogenous product (2).

TLC: system A Rf0.364 $^1$H NMR ($CDCl_3$) δ ppm: 5.67 (H-13), 4.56 (H-1"), 4.39 (H-1'), 3.90 (Ha-20), 3.58 (Hb-20), 3.61 (3"—$OCH_3$), 3.48 (2"—$OCH_3$), 2.84 (H-8), 2.49 /3'-N($CH_3$)$_2$/, 2.26 /8-N($CH_3$)$_2$/, 1.97 (H-10), 1.81 (H-22), 1.00 (H-21). $^{13}$C NMR ($CDCl_3$) δ ppm: 173.3 (C-1), 157.5 (C-11), 136.0 (C-12), 129.2 (C-13), 106.0 (C-1'), 101.0 (C-1"), 61.8 (3"—$OCH_3$), 60.8 (C-20), 59.6 (2"—$OCH_3$), 57.2 (C-8), 41.8 /3'-N($CH_3$)$_2$/, 39.6 /8-N($CH_3$)$_2$/, 36.7 (C-7), 36.2 (C-6), 13.6 (C-22), 11.5 (C-21), 10.7 (C-10).

FAB (MH) 822.

EXAMPLE 3

4'-Demicarosyl-10,12,13-trihydro-11-dehydro-11-hydroxyimino-9-carbonyl-9-nor-8a,9seco-8a-aza-8a-homorelomycin (3)

The compound 1 (0.50 g, 0.63 mmole) was dissolved in ethanol (50 ml), 10% Pd/C (0,3 g) was added and it was hydrogenated for 8 hours at room temperature and at $H_2$ pressure 0.5 MPa. The reaction mixture was filtered, the filtrate was evaporated to a dry residue, which was then chromatographed on a silica gel column using the solvent system $CHCl_3$-$CH_3OH$-conc.$NH_4OH$, 90:15:1.5, yielding 0.34 g of the TLC homo geneous product (3).

M.p. 78–83 ° C. IR (KBr) $cm^{-1}$: 1725, 1630, 1458, 1379, 1169, 1083, 960. $^1$H NMR (DMSO) δ ppm: 10.34 (11-NOH) exchangeable with $D_2O$, 4.41 (H-1'), 4.19 (H-1'), 3.45 (3"—$OCH_3$), 3.41 (2"—$OCH_3$), 3.11 (H-12), 2.75 (H-8), 2.41 /3'-N($CH_3$)$_2$/, 1.66 (H-10), 0.99 (H-21). $^{13}$C NMR (DMSO) δ ppm: 171.7 (C-1), 158.5 (C-11), 104.6 (C-1'), 100.3 (C-1"), 61.2 (3"—$OCH_3$), 59.8 (C-20), 58.1 (2"—$OCH_3$), 44.5 (C-8), 41.7 /3'-N($CH_3$)$_2$/, 38.9 (C-12), 30.8 (C-13), 24.2 (C-21), 18.9 (C-22), 10.7 (C-10).

FAB ($MH^+$) 796.

EXAMPLE 4

4'-Demicarosyl-10-hydro-11-dehydro-11-oxo-9-carbonyl-9-nor-8a,9seco-8a-aza-8a-homorelomycin (4)

The compound 1 (1.0 g, 1.26 mmole) was dissolved in 50%o ethanol (25 ml), $NaHSO_3$ (0.625 g) and formic acid (98–100%) (0.125 ml) were added and then under stirring refluxed for 6 hours. Upon addition of $H_2O$ (50 ml), a product was isolated by means of gradient extraction with $CHCl_3$ at pH 5.8 and 9.0. The combined chloroform extracts at pH 9.0 were dried ($K_2CO_3$) and evaporated at a reduced pressure, yielding 0,75 g (76.5%) of the TLC homogeneous product (4).

M.p. 67–72° C. TLC: system A Rf0.254 IR ($CHCl_3$) $cm^{-1}$: 1730, 1660, 1455, 1380, 1170, 1070, 960. $^1$H NMR ($CDCl_3$) δ ppm: 6.57 (H-13), 4.55 (H-1"), 4.36 (H-1'), 3.82 (Ha-20), 3.58 (Hb-20), 3.61 (3"—$OCH_3$), 3.44 (2"—$OCH_3$), 3,00 (H-8), 2.50 /3'-N($CH_3$)$_2$2.34 (H-10), 1.81 (H-22), 1.15 (H-21).

$^{13}$C NMR ($CDCl_3$) δ ppm: 200.0 (C-11), 172.2 (C-1), 140.2 (C-13), 140.1 (C-12), 105.4 (C-1'), 100.6 (C-1"), 61.4 (3"—$OCH_3$), 60.0 (C-20), 59.0 (2"—$OCH_3$), 44.0 (C-8), 41.4 /3'-N($CH^+$)$_2$/, 40.4 (C-7), 33.7 (C-6), 25.4 (C-10), 24.9 (C-21), 11.4 (C-22).

FAB ($MH^+$) 779.

| Analysis: | calc.: | found: |
|---|---|---|
| N | 3.60% | 3.16% |

EXAMPLE 5

4'-Demicarosyl-8a-N-formyl-8a-amino-10-hydro-11-dehydro-11-oxo-9-carbonyl-9-nor-8a,9seco-8a-aza-8a-homorelomycin (5)

The compound 4 (0.22 g, 0.28 mmole) was dissolved in $CHCl_3$ (100 Ml), formic acid (89–100%) (0.125 ml, 3.3 mmoles) was added and then it was refluxed under stirring for 16 hours. Upon addition of H$_2$O (20 ml), a product was isolated by means of gradient extraction with CHCl$_3$ at pH 5.0 and 8.5. The combined chloroform extracts at pH 8.5 were dried (K$_2$CO$_3$) and evaporated at a reduced pressure, the obtained product was chromatographed on a silica gel column using the solvent system CH$_2$Cl$_2$—CH$_3$OH-conc.NH4OH, 90:20:2, yielding 0.12 g of the TLC homogeneous product (5).

M.p. 80–85 °C. TLC: system A Rf0.538 CH$_2$Cl$_2$—CH$_3$OH (85:15), system B Rf0.071 IR(CHCl$_3$)cm$^{-1}$: 1715, 1660, 1530, 1445, 1375, 1160, 1060, 955.

$^1$H NMR (CDCl$_3$) δ ppm: 8.13 (HCONH), 6.38 (CONH) exchangeable with D$_2$O, 6.64 (H-13), 4.56 (H-1"), 4.33 (H-1'), 4.15 (H-8), 3.70 (Ha-20), 3.66 (Hb-20), 3.61 (3"—OCH$_3$), 3.45 (2"—OCH$_3$), 2.55 /3'-N(CH$_3$)$_2$/, 2.34 (H-10), 1.80 (H-22), 1.19 (H-21)

$^{13}$C NMR (CDCl$_3$) δ ppm: 200.4 (C-11), 172.7 (C-1), 161.7 (HCONH), 141.2 (C-13) 140.0 (C-12), 104.9 (C-1'), 100.7 (C-1"), 61.5 (3"—OCH$_3$), 59.8 (C-20), 59.1 (2"—OCH$_3$), 41.9 (C-8), 41.5 /3'-N(CH$_3$)$_2$/, 37.0 (C-7), 32.2 (C-6), 25.6 (C-10), 21.7 (C-21), 11.4 (C-22).

FAB (MH') 807.

EXAMPLE 6

4'-Demicarosyl-10-hydro-11-hydroxy-9-carbonyl-9-nor-8a,9seco-8a-aza-8a-homorelomycin (6)

The compound 4 (0.60 g, 0.77 mmole) was dissolved in abs. CH$_3$OH (20 ml), under stirring during 5 minutes NaBH$_4$ (0.06 g) was added and then the reaction mixture was kept stirring for 1 hour at room temperature. After evaporation of the solvent to one half of its volume, H$_2$O (20 ml) and CHCl$_3$ (40 ml) were added to the reaction mixture and with 1 N HCl, the pH was adjusted to 9.0. The layers were separated and the aqueous part was extracted twice with CHCl$_3$. The combined chloroform extracts were rinsed with saturated NaHCO$_3$, dried (K$_2$CO$_3$) and evaporated at a reduced pressure, yielding 0.59 g (98.08%) of the TLC homogeneous product (6).

M.p. 64–68° C. TLC: system A Rf0.159 IR(CHCl3) cm$^{-1}$: 1730, 1600, 1455, 1380, 1170, 1070, 960.

$^1$H NMR (CDCl$_3$) δ ppm: 5.34 (H-13), 4.49 (H-1"), 4.28 (H-1'), 4.08 (H-11), 3.74 (Ha-20), 3.60 (Hb-20), 3.53 (3"—OCH$_3$), 3.41 (2"—OCH$_3$), 2.90 (H-8), 2.78 (H-14), 2.42 /3'-N(CH$_3$)$_2$/, 1.56 (H-22), 1.14 (H-10), 1.06 (H-21).

$^{13}$C NMR (CDCl$_3$) δ ppm: 171.9 (C-1), 142.9 (C-12), 119.8 (C-13), 105.3 (C-1'), 100.3 (C-1"), 72.4 (C-11), 61.4 (3"—OCH$_3$), 59.8 (C-20), 59.2 (2"—OCH$_3$), 43.9 (C-8), 41.5 /3'-N(CH$_3$)$_2$/, 41.3 (C-14), 39.9 (C-7), 33.2 (C-6), 32.2 (C-19), 25.5 (C-21), 21.4 (C-10), 13.1 (C-22).

FAB (MH$^+$) 781.

EXAMPLE 7

4'-Demicarosyl-8a-N-tosyl-10-hydro-11-hydroxy-9-carbonyl-9-nor-8a,9seco-8a-aza-8a-homorelomycin (7)

The compound 4 (0.23 g, 0.3 mmole) was dissolved in dry pyridine (20 ml) and cooled to 0–5° C. Into the reaction mixture under stirring a solution of tosylchloride (0.2 g, 1.05 mmole) in dry pyridine (10 ml) was added dropwise during 5 minutes and it was stirred for further 2 hours at room temperature. The reaction solution was diluted with H$_2$O (120 ml), alkalized to 9.5 by addition of 10% w/AT NaOH, evaporated at a reduced pressure to one third of its volume and extracted twice with CHCl$_3$. The combined chloroform extracts were evaporated to a resin-like residue, which was chromatographed on a silica gel column using the solvent system CH$_2$Cl$_2$—CH$_3$OH, 85:15, yielding 0.14 g of the TLC homogeneous product (7).

M.p. 78–83° C. TLC: system A Rf0.671 system B Rf0.077 IR (CHCl$_3$) cm$^{-1}$: 1720, 1600, 1645, 1450, 1380, 1325, 1170, 1070, 960.

$^1$H NMR (CDCl$_3$) δ ppm: 7.76 (p-Ph), 7.32 (SO$_2$NH), 5.82 (H-13), 5.42 (H-1"), 4.56 (H-1'), 4.21 (H-11), 3.60 (3"—OCH$_3$), 3.49 (2"—OCH$_3$), 2.50 /3'-N(CH$_3$)$_2$/, 2.43 (p-Ph-CH$_3$), 1.66 (H-22), 1.02 (H-21).

FAB (MH$^+$) 935.

EXAMPLE 8

4'-Demicarosyl-10,12,13-trihydro-11-dehydro-11-oxo-9-carbonyl-9-nor-8a,9seco-8a-aza-8a-homorelomycin (8)

The compound 4 (0.3 g, 0.39 mmole) was dissolved in ethanol (25 ml), 10% Pd/C (0.15 g) was added and it was hydrogenated for 8 hours at room temperature and at H$_2$ pressure of 0.3 MPa. The reaction mixture was filtered, the filtrate was evaporated to a dry residue, which was then chromatographed on a silica gel column using the solvent system CH$_2$Cl$_2$—CH$_3$OH-conc.NH$_4$OH, 90:20:2, yielding 0.2 g of the TLC homogeneous product (8).

M.p. 69–73° C. TLC: system A Rf0.211 IR (CHCl$_3$) cm$^{-1}$: 1715, 1700, 1440, 1370, 1155, 1070, 950.

$^1$H NMR (CDCl$_3$) δ ppm: 4.55 (H-1"), 4.38 (H-1'), 3.62 (3"—OCH$_3$), 3.51 (2"—OCH$_3$), 3.11 (H-12), 2.75 (H-8), 2.49 /3'-N(CH$_3$)$_2$/, 2.17 (H-10), 1.79 (H-14), 1.42 (Hb-13), 1.18 (H-22), 1.12 (H-21).

FAB (MH$^+$) 781.

EXAMPLE 9

4'-Demicarosyl-10,12,13-trihydro-11-hydroxy-9-carbonyl-9-nor-8a,9seco-8a-aza-8a-homorelomycin (9)

The compound 6 (0.46 g, 0.59 mmole) was dissolved in ethanol (25 ml), 10% Pd/C (0.15 g) was added and it was hydrogenated for 4 hours at room temperature and at H$_2$ pressure of 0.5 MPa. The isolation of the product was carried out as described in Example 8, yielding 0.34 g of the TLC homogeneous product (9).

M.p. 76–83° C. TLC: system A Rf0.176 IR (CHCl$_3$)cm$^{-1}$: 1725, 1600, 1455, 1380, 1265, 1170, 1070.

$^1$H NMR (CDCl$_3$) δ ppm: 4.55 (H-1"), 4.36 (H-1'), 4.08 (H-11), 3.80 (Ha-20), 3.78 (H-12), 3.65 (Hb-20), 3.62 (3"—OCH$_3$), 3.51 (2"—OCH$_3$), 3.12 (H-8), 2.49 /3'-N(CH$_3$)$_2$/, 2.17 (H-10), 1.79 (H-14), 1.54 (Hb-13), 1.21 (H-10), 1.19 (H-21), 1.11 (H-22).

$^{13}$C NMR (CDCl$_3$) δ ppm: 172.7 (C-1), 105.0 (C-1'), 100.5 (C1"), 61.5 (3"—OCH$_3$) 59.9 (C-20), 59.1 (2"—OCH$_3$), 44.4 (C-8), 41.5 /3'-N(CH$_3$)$_2$/, 39.9 (C-13), 36.8 (C-12), 23.8 (C-21), 21.5 (C-10).

FAB (MH$^+$) 783.

EXAMPLE 10

4'-Demicarosyl-8a-N,2', 4'-O-triacetyl-10-hydro-11-dehydro-11-oxo-9-carbonyl-9-nor-8a,9seco-8a-aza-8a-homorelomycin (10)

The compound 6 (0.60 g, 0.77 mmole) was dissolved in CH$_2$Cl$_2$ (15 ml), acetic acid anhydride (0.36 ml) was added and it was stirred for 1 hour at room temperature. The reaction mixture was poured onto ice (50 ml) and extracted with $CH_2Cl_2$ at pH 8.0. The combined organic extracts were rinsed with a saturated $NaHCO_3$ solution and water, dried ($K_2CO_3$) and evaporated at a reduced pressure, yielding 0.65 g (93.3%) of the TLC homogeneous product (10).

M.p. 74–78° C. TLC: system A Rf0.809 system B Rf0.665 IR (KBr)cm$^{-1}$: 1750, 1660, 1550, 1455, 1375, 1230, 1170, 1060, 960.

$^1$H NMR (CDCl$_3$) δ ppm: 6.50 (H-13), 6.12 (CONH) exchangeable with D$_2$O, 4.82 (H-2'), 4.68 (H-4'), 4.49 (H-1"), 4.38 (H-1'), 4.00 (H-8), 3.54 (3"—OCH$_3$), 3.36 (2"—OCH$_3$), 2.27 /3'-N(CH$_3$)$_2$/, 1.99, 1.99 and 1.97 (COCH$_3$), 1.86 (H 10), 1.76 (H-22), 1.20 (H-21).

$^{13}$C NMR (CDCl$_3$) δ ppm: 199.9 (C-11), 172.4 (C-1), 170.9, 169.8 and 169.4 (COCH$_3$), 140.4 (C-13), 139.6 (C-12), 101.8 (C1'), 100.6 (C-1"), 61.5 (3"—OCH$_3$), 59.7 (C-20), 59.0 (2"—OCH$_3$), 42.9 (C-8), 41.0 /3'-N(CH$_3$)$_2$/, 37.0 (C-7), 25.4 (C-10), 22.8 (C-21), 21.6, 21.0 and 20.9 (COCH$_3$), 11.6 (C-22).

FAB (MH$^+$) 905.

EXAMPLE 11

4'-Demicarosyl-8a-N-acetyl-10-hydro-11-dehydro-11-oxo-9-carbonyl-9-nor-8a,9seco-8a-aza-8a-homorelomycin (11)

The compound 10 (0.3 g, 0.33 mmole) was dissolved in CH$_3$OH (15 ml) and stirred for 3 days at room temperature. By evaporation at a reduced pressure the solvent was removed and the obtained product was purified by chromatography on a silica gel column using the solvent system CH$_2$Cl$_2$—CH$_3$OH-conc.NH$_4$OH, 90:20:2, yielding 0.18 g of the TLC homogeneous product (11).

M.p. 70–74° C. TLC: system A Rf0.540 system B Rf0.077

$^1$H NMR (CDCl$_3$) δ ppm: 6.59 (H-13), 6.17 (CONH) exchangeable with D$_2$O, 4.56 (H-1"), 4.32 (H-1'), 4.08 (H-8), 3.61 (3"—OCH$_3$), 3.56 (H-2'), 3.45 (2"—OCH$_3$), 3.02 (H-4'), 2.53 /3'-N(CH$_3$)$_2$/, 2.34 (H-10), 1.96 (COCH$_3$), 1.81 (H-22), 1.16 (H-21).

FAB (MH$^+$) 821.

EXAMPLE 12

4'-Demicarosyl-8a-dimethylamino-10,12,13-trihydro-11-hydroxy-9-carbonyl-9-nor-8a,9seco-8a-aza-8a-homorelomycin (12)

To a solution of the compound 9 (0.20 g, 0.256 mmole) in chloroform (40 ml) cooled to 15° C., formic acid (98–100%) (0.02 ml, 0.52 mmole) and formaldehyde (36%) (0.04 ml, 0.54 mmole) were added and the reaction mixture was stirred at the same temperature for 4 hours. After additon of H$_2$O (80 ml), a product was isolated by gradient extraction with CHCl$_3$ at pH 5.5 and 9.0. The combined chloroform extracts at pH 9.0 were dried (K$_2$CO$_3$) and evaporated at a reduced pressure, yielding 0.195 g (93.2%) of the TLC homogeneous product (12).

M.p. 56–61° C. TLC: system A Rf0.250 IR (KBr)cm$^{-1}$: 1730, 1640, 1460, 1380, 1260, 1170, 1080, 960.

$^1$H NMR (CDCl$_3$) δ ppm: 4.48 (H-1"), 4.28 (H-1'), 4.13 (H-11), 3.78 (H-12), 3.70 (Ha-20), 3.62 (Hb-20), 3.55 (3"—OCH$_3$), 3.45 (2"—OCH$_3$), 2.68 (H-8), 2.42 /3'-N(CH$_3$)$_2$/, 2.12 (H-10), 1.84 (H-14), 1.46 (Ha-13), 1.14 (Hb-13), 1.09 (H-10), 1.06 (H-22), 0.85 (H-21). $^{13}$C NMR (CDCl$_3$) δ ppm: 172.9 (C-1), 105.7 (C-1'), 100.5 (C-1"), 61.5 (3"—OCH$_3$) 60.3 (C-20), 59.3 (2"—OCH$_3$), 55.8 (C-8), 41.5 /3'-N(CH$_3$)$_2$/, 39.4 /8-N-(CH$_3$)$_2$/, 36.4 (C-7), 19.6 (C-22), 11.3 (C-21).

FAB (MH$^+$) 811.

EXAMPLE 13

4'-Demicarosyl-8a-dimethylamino-10-hydro-11-hydroxy-9-carbonyl-9-nor-8a,9seco-8a-aza-8a-homorelomycin (13)

To a solution of the compound 6 (0.20 g, 0.256 mmole) in chloroform (40 ml) cooled to 15° C., formic acid (98–100%) (0.02 ml, 0.52 mmole) and formaldehyde (36%) (0.04 ml, 0.54 mmole) were added and the reaction mixture was stirred at the same temperature for 4 hours and then at room temperature for 20 hours. The isolation of the product was carried out as described in the Example 12, yielding 0.192 g (92.6%) of the TLC homogeneous product (13).

TLC: system A Rf0.295 IR (KBr)cm$^{-1}$: 1730, 1640, 1455, 1380, 1260, 1170, 1090. $^1$H NMR (CDCl$_3$) δ ppm: 5.37 (H-13), 4.49 (H-1"), 4.28 (H-1'), 4.11 (H-11), 3.72 (Ha-20), 3.60 (Hb-20), 3.53 (3"—OCH$_3$), 3.41 (2"—OCH$_3$), 2.75 (H-14), 2.42 /3'-N(CH$_3$)$_2$/, 2.11 /8-N(CH$_3$)$_2$/, 1.56 (H-22), 1.14 (H- 10), 0.82 (H-21).

FAB (MH$^+$) 810.

EXAMPLE 14

4'-Demicarosyl-10,12,13-trihydro-11-dehydro-11-amino-9-carbonyl-9-nor-8a,9seco-8a-aza-8a-homorelomycin (14)

The compound 1 (0.40 g, 0.5 mmole) was dissolved in glacial acetic acid (30 ml), PtO$_2$ (83% Pt) (0.20 g) was added and then it was hydrogenated under stirring at room temperature and at the H$_2$ pressure of 40.53 bars for 30 hours. The reaction suspension was filtered, the filtrate was evaporated at a reduced pressure to a thick oily residue, H$_2$O (60 ml) and CHCl$_3$ (30 ml) were added and it was extracted by gradient extraction at pH 5.5, 7.5 and 9.5. The combined chloroform extracts at pH 9.5 were dried (K$_2$CO$_3$) and evaporated at a reduced pressure, yielding 0.32 g (80.5%) of the TLC homogeneous product (14).

M.p. 85–89° C. IR (KBr) cm–1: 1724,1597, 1459, 1379, 1263,1168, 1084.

$^1$H NMR (CDCl$_3$) δ ppm: 4.52 (H-1"), 4.34 (H-1'), 3.62 (3"—OCH$_3$), 3.51 (2"—OCH$_3$), 3.35 (H-8), 3.11 (H-11), 2.49 /3'-N(CH$_3$)$_2$/, 1.72 (H-12), 1.48 (Hb-13), 1.19 (H-21), 1.12 (H-10), 0.94 (H-22).

$^{13}$C NMR (CDCl$_3$) δ ppm: 173.7 (C-1), 105.0 (C-1'), 100.5 (C-1"), 61.5 (3"—OCH$_3$), 59.9 (C-20), 59.1 (2"—OCH$_3$), 50.3 (C-11), 45.0 (C-8), 41.5 /3'-N(CH$_3$)$_2$/, 36.9 (C-13), 35.9 (C-12), 17.5 (C-10), 14.9 (C-22).

FAB (MH$^+$) 782.

EXAMPLE 15

4'-Demicarosyl-10-hydro-11-dehydro-11-amino-9-carbonyl-9-nor-8a,9seco-8a-aza-8a-homorelomycin (15)

The compound 1 (0.30 g, 0.38 mmole) was dissolved in a phosphate buffer pH 5.8 (50 ml) and electrolytically reduced in a 100 ml cell, whereat through a catholyte nitrogen was introduced, at a constant potential of 1.2 V at room temperature. The reaction was carried out on a mercury cathode placed on the bottom of the cell next to a graphite anode for 2 hours, whereat 3.4 Faradays were used.

To the reaction mixture CHCl₃ was added and a product was isolated by gradient pH extraction at pH 6.5 and 10.0. The combined chloroform extracts at pH 10.0 were dried (K₂CO₃) and evaporated at a reduced pressure, yielding 0.22 g (73.3%) of the TLC homogeneous product (15).

M.p. 64–68° C. IR (KBr)cm⁻¹: 1722, 1638, 1458, 1379, 1169, 1084.

¹H NMR (CDCl₃) δ ppm: 5.28 (H-13), 4.55 (H-1"), 4.36 (H-1'), 3.62 (3"—OCH₃), 3.51 (2"—OCH₃), 3.01 (H-8), 2.49 /3'-N(CH₃)₂/, 2.88 (H-11), 1.64 (H-22), 1.12 (H-21), 1.01 (H-10).

¹³C NMR (CDCl₃) δ ppm: 172.5 (C-1), 143.4 (C-12), 120.6 (C-13), 105.5 (C-1'), 100.5 (C-1"), 61.4 (3"—OCH₃), 60.0 (C-20), 59.1 (2"—OCH₃), 53.9 (C-11), 44.4 (C-8), 41.4 /3'-N(CH₃)₂/, 21.8 (C-21), 12.1 (C-22).

FAB (MH⁺) 780.

We claim:

1. Compounds represented by a general formula I

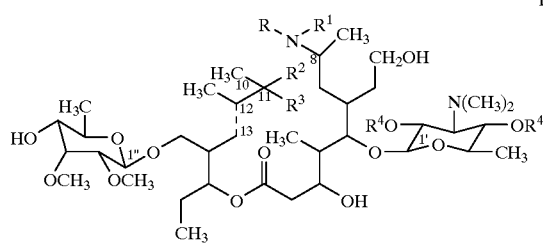

wherein,

R stands for H or CH₃,

R¹ stands for H, CH₃, C₁–C₃ acyl or aryl sulfonyl,

R² stands for H and R³ stands for NH₂ or OH, or R² and R³ together stand for =O or NOH, R⁴ stands for H or C₁–C₃ acyl, and the line - - - stands for a double or a single bond.

2. A compound according to claim 1, wherein R, R¹ and R⁴ are the same and stand for H, R² and R³ together stand for =NOH and the line - - - stands for a double bond.

3. A compound according to claim 1, wherein R and R¹ are the same and stand for CH₃, R² and R³ together stand for =NOH, R⁴ stands for H and the line - - - stands for a double bond.

4. A compound according to claim 1, wherein R and R¹ are the same and stand for CH₃, R² and R³ together stand for =NOH, R⁴ stands for H and the line - - - stands for a single bond.

5. A compound according to claim 1, wherein R, R¹ and R⁴ are the same and stand for H, R² and R³ together stand for =O and the line - - - stands for a double bond.

6. A compound according to claim 1, wherein R and R⁴ are the same and stand for H, R¹ stands for formyl group, R² and R³ together stand for =O and the line - - - stands for a double bond.

7. A compound according to claim 1, wherein R, R¹, R² and R⁴ are the same and stand for H, R³ stands for OH and the line - - - stands for a double bond.

8. A compound according to claim 1, wherein R, R² and R⁴ are the same and stand for H, R¹ stands for tosyl group, R³ stands for OH and the line - - - stands for a double bond.

9. A compound according to claim 1, wherein R, R¹ and R⁴ are the same and stand for H, R² and R³ together stand for =O and the line - - - stands for a single bond.

10. A compound according to claim 1, wherein R, R¹, R² and R⁴ are the same and stand for H, R³ stands for OH and the line - - - Stands for a single bond.

11. A compound according to claim 1, wherein R stands for H, R¹ and R⁴ are the same and stand for an acetyl group, R² and R³ together stand for =O and the line - - - stands for a double bond.

12. A compound according to claim 1, wherein R and R⁴ are the same and stand for H, R¹ stands for an acetyl group, R² and R³ together stand for =O and the line - - - stands for a double bond.

13. A compound according to claim 1, wherein R and R¹ are the same and stand for CH₃, R² and R⁴ are the same and stand for H, R³ stands for OH and the line - - - stands for a single bond.

14. A compound according to claim 1, wherein R and R¹ are the same and stand for CH₃, R² and R⁴ are the same and stand for H, R³ stands for OH and the line - - - stands for a double bond.

15. A compound according to claim 1, wherein R, R¹, R² and R⁴ are the same and stand for H, R³ stands for NH₂ and the line - - - stands for a double bond.

16. A compound according to claim 1, wherein R, R¹, R² and R⁴ are the same and stand for H, R³ stands for NH₂ and the line - - - stands for a single bond.

17. Process for the preparation of compounds of a general formula I

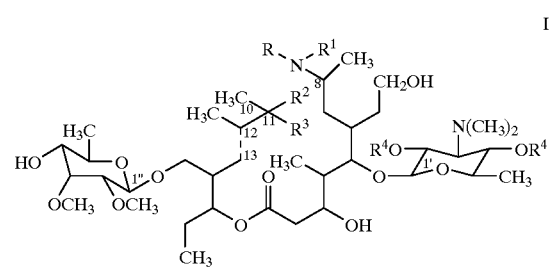

wherein

R stands for H or CH₃,

R¹ stands for H, CH₃, C₁–C₃ acyl or aryl sulfonyl,

R² stands for H and R³ stands for NH₂ or OH, or R² and R³ together stand for =O or =NOH, R⁴ stands for H or C₁–C₃ acyl, and the line - - - stands for a double or a single bond, wherein 4'-demicarosyl-8a-aza-8a-homorelomycin of the formula II

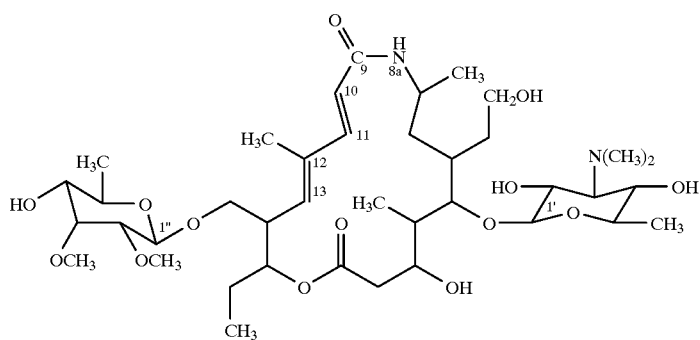

is subjected to
- A/ oximation with 3–10 equivalents of hydroxlyamine hydrochloride in pyridine in a nitrogen stream at reflux temperature during 3 to 10 hours, whereby a compound of formula I is obtained, wherein R, $R^1$ and $R^4$ are the same and stand for H, $R^2$ and $R^3$ together stand for =NOH and the line - - - stands for a double bond which is then optionally
- A1/ reductively N-alkylated with 1–4 equivalents of formaldehyde (36% w/v) in the presence of the 1–5 equivalents of formic acid (98–100% wv) in halogenated hydrocarbons, such as chloroform or methylene chloride, at a temperature from 10° C. to reflux temperature during 2 to 30 hours, whereby a compound of formula I is obtained, wherein R and $R^1$ are the same and stand for $CH_3$, $R^2$ and $R^3$ together stand for =NOH, $R^4$ stands for H and the line - - - stands for a double bond;
- or a compound obtained by process A is, optionally, subjected to
- A2/ a catalytic hydrogenation in $C_1$–$C_3$ aliphatic alcohol in the presence of a noble metal on an inert carrier at a hydrogen pressure from 0.2 to 0.5 MPa and at room temperature during 2 to 10 hours, whereby a compound of formula I is obtained, wherein R, $R^1$ and $R^4$ are the same and stand for H, $R^2$ and $R^3$ together stand for =NOH and the line - - - stands for a single bond;
- or a compound obtained by process A is optionally subjected to
- B/ conversion of hydroxyimino group into keto group with $NaHSO_3$ in the presence of an acid in 50% ethanol, at reflux temperature during 2 to 8 hours, whereby a compound of formula I is obtained wherein R, $R^1$ and $R^4$ are the same and stand for H, $R^2$ and $R^3$ together stand for =O and the line - - - stands for a double bond, which is then optionally subjected to
- B1/ a reaction of N- or N,O-acylation with $C_1$–$C_3$ carboxylic acids in a halogenated hydrocarbon at room temperature or reflux temperature during 1 to 20 hours, whereby a compound of a general formula I is obtained, wherein R and $R^4$ are the same and stand for H, $R^1$ stands for CHO, $R^2$ and $R^3$ together stand for =O and the line - - - stands for a double bond, and a compound of the formula I, wherein R stands for H, $R^1$ and $R^4$ are the same and stand for $COCH_3$, $R^2$ and $R^3$ together stand for =O and the line - - - stands for a double bond, which is then optionally subjected to
- B1/1 methanolysis at room temperature during 3 days, yielding a compound of a general formula I, wherein R and $R^4$ are the same and stand for H, $R^1$ stands for $COCH_3$, $R^2$ and $R^3$ together stand for =O and the line - - - stands for a double bond;
- or a compound obtained by process B is optionally subjected to
- B2/ catalytic hydrogenation in the manner described in A2, whereby a compound of formula I is obtained, wherein R, $R^1$ and $R^4$ are the same and stand for H, $R^2$ and $R^3$ together stand for =O and the line - - - stands for a single bond;
- or a compound obtained by process B is optionally, subjected to
- C/ a reduction with $NaBH_4$ in a $C_1$–$C_3$ aliphatic alcohol at room temperature during 0.5 to 2 hours, whereby a compound of formula I is obtained, wherein R, $R^1$, $R^2$ and $R^4$ are the same and stand for H, $R^3$ stands for OH and the line - - - stands for a double bond, which is optionally subjected to
- C1/ N-tosylation with p-toluene sulfochloride in pyridine at room temperature during 1 to 5 hours, whereby a compound of formula I is obtained, wherein R, $R^2$ and $R^4$ are the same and stand for H, $R^1$ stands for tosyl, $R^3$ stands for OH and the line - - - stands for a double bond,
- or a compound obtained by process C is optionally subjected to
- C2/ reductive N-alkylation in the manner described in A1, whereby a compound of formula I is obtained, wherein R and $R^1$ are the same and stand for $CH_3$, $R^2$ and $R^4$ are the same and stand for H, $R^3$ stands for OH and the line - - - stands for a double bond;
- or a compound obtained by process C is optionally subjected to
- C3/ catalytic hydrogenation in the manner described in A2, whereby a compound of formula I is obtained, wherein R, $R^1$, $R^2$ and $R^4$ are the same and stand for H, $R^3$ stands for OH and the line - - - stands for a single bond, which is optionally
- C4/ N-alkylated in the manner described in A1, whereby a compound of formula I is obtained, wherein R and $R^1$ are the same and stand for $CH_3$, $R^2$ and $R^4$ are the same and stand for H, $R^3$ stands for OH and the line - - - stands for a single bond;
- or a compound obtained by process A is optionally
- D/ subjected to catalytic reduction in glacial acetic acid in the presence of noble metals and their oxides as catalysts at a hydrogen pressure from 5.07 to 70.93 bars and at room temperature during 10 hours to 3 days, whereby a compound of formula I is obtained, wherein R, $R^1$, $R^2$ and $R^4$ are the same and stand for H, $R^3$ stands for $NH_2$ and the line - - - stands for a single bond;

or a compound obtained by process A is optionally subjected to

E/ an electrochemical reduction in an electrolytic H-cell with anode and cathode regions separated by a membrane, using a Hg basin as the working electrode and graphite as the counter electrode, in a phosphate buffer with pH 4.0–7.0 at a constant potential between 1.2–1.6 V against saturated calomel electrode during 1 to 5 hours at room temperature in a nitrogen stream, whereby a compound of formula I is obtained, wherein R, $R^1$, $R^2$ and $R^4$ are the same and stand for H, $R^3$ stands for $NH_2$ and line - - - stands for a double bond.

18. The process of claim 17 wherein step A2 is carried out in the presence of palladium-on-charcoal 2–5% w/w).

19. The process of claim 17 wherein the acid in step B is formic acid (98–100% w/w).

20. The process of claim 17 wherein the halogenated hydrocarbon in step B1 is chloroform or methylene chloride.

21. The process of claim 17 wherein step D is carried out in the presence of platinum (IV) oxide.

* * * * *